United States Patent [19]
Taylor

[11] 4,083,370
[45] Apr. 11, 1978

[54] BLOAT RELIEF TUBE AND HOLDER

[76] Inventor: John D. Taylor, Rte. 3 Box 16, Perryton, Tex. 79070

[21] Appl. No.: 738,191

[22] Filed: Nov. 3, 1976

[51] Int. Cl.² .............................................. A61B 17/34
[52] U.S. Cl. ................................. 128/347; 128/350 R
[58] Field of Search ................... 128/347, 350 R, 356, 128/214.4

[56] References Cited

U.S. PATENT DOCUMENTS

| 1,147,408 | 7/1915 | Kells | 128/347 |
| 1,640,311 | 8/1927 | Dawes | 128/347 X |
| 3,039,468 | 6/1962 | Price | 128/347 |
| 3,570,498 | 3/1971 | Weighton | 128/347 |
| 3,717,151 | 2/1973 | Collett | 128/347 |

FOREIGN PATENT DOCUMENTS 157,460  3/1962  U.S.S.R. ................................ 128/347

Primary Examiner—Robert W. Michell
Assistant Examiner—Michael H. Thaler
Attorney, Agent, or Firm—Robert K. Rhea

[57] ABSTRACT

An elongated plunger is slidably connected at one end with one end of a sleeve for telescoping movement into the sleeve. The other end portion of the sleeve releasably supports a cannula to be inserted at one end through the skin and stomach wall of a bloated animal. Flexible wing members on the pointed end portion of the cannula normally maintains the inserted end portion of the cannula within the animal's stomach. A stop, slidably surrounding the other end portion of the cannula, maintains one end portion of the cannula projecting outwardly of the animal's skin.

2 Claims, 5 Drawing Figures

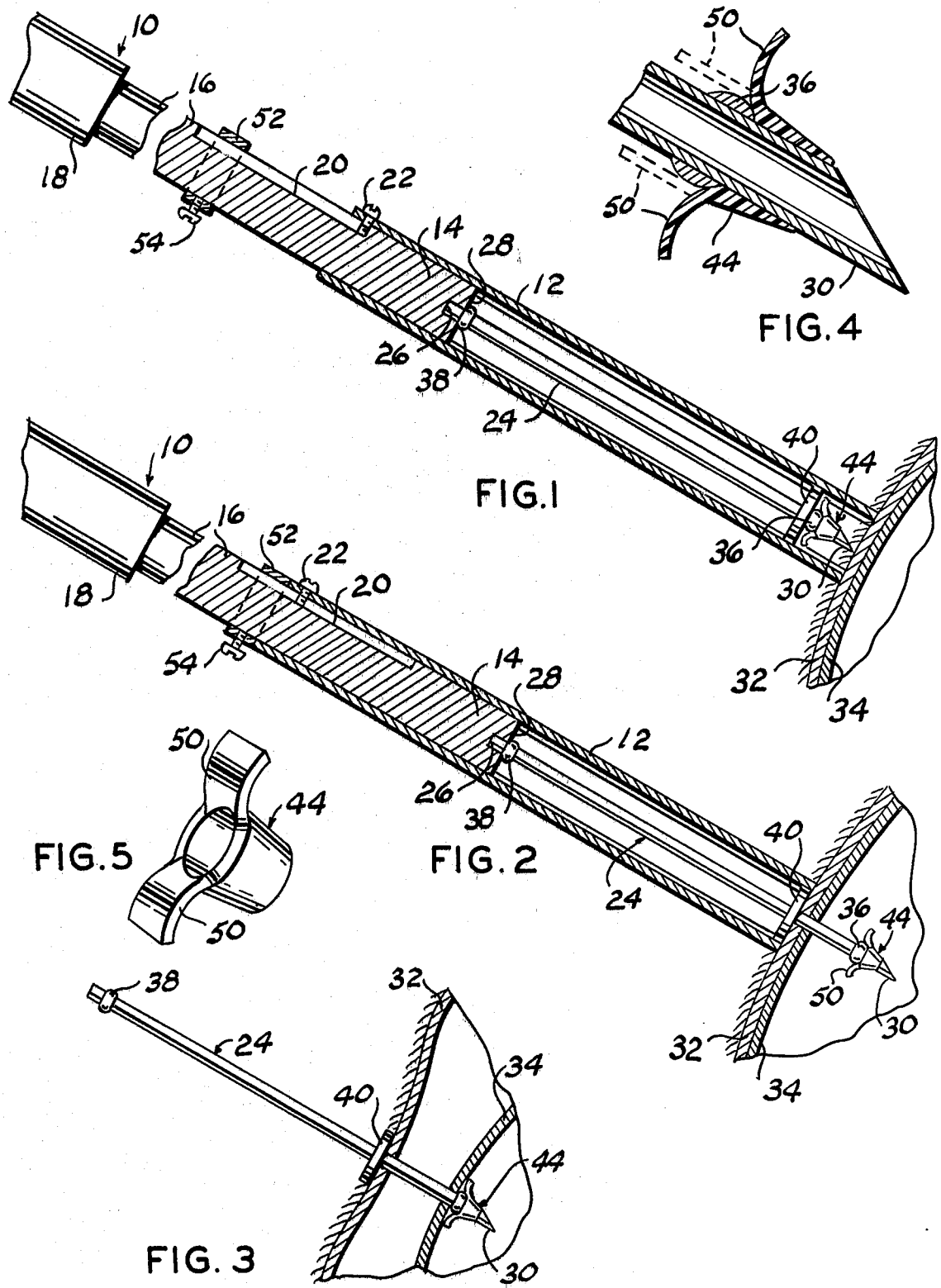

BLOAT RELIEF TUBE AND HOLDER

BACKGROUND OF THE INVENTION

1. Field of the Invention

The present invention relates to veterinary instruments and more particularly to a bloat relief tube.

Under certain conditions cattle grazing on green foliage become bloated as a result of gas or foam accumulating in the rumen or first stomach which causes a distention of the rumen and a swelling of the animal most prominently on the left side. When bloat occurs it is necessary to promptly release the gas or the condition may prove to be fatal. Range cattle when running loose in the field are not easily caught or controlled for treatment of bloat for the reason they will run from or attempt to fight a man on foot, however, a man on horseback can get relatively close to a bloated animal.

Trocar devices for the treatment of bloat presently available are usually of relatively short length and require some manipulation after being inserted into a bloated animal and for this reason are not capable of being used by a man on horseback attempting to relieve a bloated condition.

2. Description of the Prior Art

As mentioned hereinabove, trocar devices are disclosed by the prior art, such as U.S. Pat. Nos. 387,480 and 3,039,468, are usually of relatively short length, such length being insufficient to permit the device to be installed or manipulated while on horseback.

It is usually impractical to attempt to move the animal to a holding chute, or the like, for the reason the animal may be several miles from the nearest holding chute and sufficient time is seldom available for such movement of the animal. The time elapsing between initial and terminal stages of bloat may be on the order of one hour or less.

This invention provides a cannula which is supported by one end of a sleeve having an elongated handle equipped plunger attached to the other end of the sleeve whereby the cannula may be inserted into a bloated animal from a distance of six feet or more, the cannula being automatically released from the sleeve upon insertion through the skin and into the stomach of the animal.

SUMMARY OF THE INVENTION

An elongated rod-like plunger, preferably formed of light-weight material, is slidably connected with one end of an elongated sleeve for telescoping movement of the plunger into the sleeve. An elongated cannula is contained by the other end portion of the sleeve with one end of the cannula coaxially supported within the sleeve by the plunger and the other end of the cannula coaxially supported within the sleeve by a washer-like stop slidably contained by the sleeve. The sharpened end portion of the cannula is provided with a surrounding retainer ring having oppositely disposed wing portions to maintain the pointed end of the cannula within the stomach of the animal during and following the release of gas thus preventing entry of food stuff or gas from the stomach into the peritoneal cavity. The stop washer prevents complete entry of the cannula into the animal when the bloated condition is released and the stomach wall is disposed inwardly of the animal's skin.

The principal object of this invention is to provide a bloat relief cannula or tube supported by a sleeve with the cannula inserted by an elongated handle equipped telescoping plunger member which is quickly and easily operated and permits the user to maintain a distance between himself and the animal being treated.

BRIEF DESCRIPTION OF THE DRAWINGS

FIG. 1 is a longitudinal cross sectional view, partially in elevation, illustrating a cannula in position to be inserted through the side of a bloated animal, a fragment of the skin and stomach wall being shown in cross section;

FIG. 2 is a view similar to FIG. 1 illustrating the cannula after insertion into a bloated animal;

FIG. 3 illustrates the relative position of the cannula with respect to an animal's skin and stomach wall when the bloated condition is at least partially relieved and the manner in which the cannula is maintained in position to extend across the peritoneal cavity;

FIG. 4 is a fragmentary cross sectional view, to a larger scale, of the penetrating end portion of the cannula and illustrating, by dotted lines, the collapsed position of the cannula retainer wings when being inserted through an animal's skin; and, FIG. 5 is a perspective view of a cannula retaining ring, per se.

DESCRIPTION OF THE PREFERRED EMBODIMENT

Like characters of reference designate like parts in those figures of the drawings in which they occur.

In the drawings:

The reference numeral 10 indicates the device, as a whole, which is elongated cylindrical in general configuration. The device comprises an elongated open ended sleeve 12 surrounding one end portion 14 of a plunger 16 having a handle at its other end portion. The wall of the plunger is provided with an elongated slot 20 which slidably receives the inwardly disposed end of a screw 22 inserted through the wall of the sleeve 12. A bloat relief tube or cannula 24 is coaxially disposed within the other end portion of the sleeve 12. The diameter of the cannula 24 is relatively small, for example ¼ inch (0.63mm), and has one end portion nested by a socket 26 coaxially formed in the inwardly disposed end 28 of the plunger. The other end of the cannula has a beveled end portion forming a sharpened tip 30 for piercing the skin 32 of an animal and the wall of its stomach 34 when the cannula is forced therethrough, as presently described.

Adjacent its sharpened end 30 a first ferrule 36 surrounds the cannula. A second similar ferrule 38 surrounds the cannula adjacent the plunger end wall 28. A washer-like stop 40 slidably surrounds the cannula between the ferrules 36 and 38 within the sleeve 12 and is normally disposed adjacent the first ferrule 36 for maintaining the cannula coaxial with the forward open end 42 of the sleeve. The principal purpose of the washer 40 is for preventing complete entry of the cannula into the stomach of an animal, as presently explained. Alternatively the wall of the cannula may be externally upset or diametrically enlarged at the positions of the ferrules, if desired.

A cannula retainer ring 44 surrounds the cannula between its pointed end 30 and the first ferrule 36. The retainer ring 44 comprises a short length of plastic tubing, or the like, having a bore snuggly surrounding the periphery of the cannula. The outer wall surface of the retainer ring is tapered toward the pointed end 30 of the cannula to facilitate insertion of the cannula through an animal's skin and stomach. The end of the retainer ring, adjacent the first ferrule 36, is provided with diametrically opposite wing portions 50 normally projecting laterally of the longitudinal axis of the cannula for retaining the cannula within an animal's stomach, as presently explained.

The wing members 50 are flexible so that they may extend parallel with the wall of the cannula during the insertion of the cannula through an animal's side, as shown by dotted lines (FIG. 4). The distance of penetrating axial movement of the cannula through the animal's skin and stomach wall is governed by a stop ring 52 surrounding the plunger 14 in predetermined spaced relation with respect to the adjacent rearward end of the sleeve 12. A set screw 54 maintains the stop ring 52 in position on the plunger 14.

Operation

In operation, a rider on horseback, not shown, holds the device 10 by the handle 18 and places the sleeve forward end in contact with a bloated cow's body, usually on the left side, rearwardly of the rib cage and forwardly of the hip bones. A longitudinal force manually applied to the plunger 14 drives the pointed end portion 30 of the cannula, including the retainer ring 44 and first ferrule 36, through the cow's skin 32 and stomach wall 34, as illustrated in FIG. 2. The retainer wings 50, flexing to their dotted line position (FIG. 4), returns to their position of repose, shown by solid lines, which retains the cannula within the stomach area, axial movement of the plunger being limited by the stop ring 52 during this action. The plunger and sleeve when axially withdrawn off the cannula leaves the cannula 24 inserted into the cow's side wherein the washer 40 prevents the cannula moving completely through the cow's skin by reason of the stop washer contacting the second ferrule 38. As the bloating gas is released through the bore of the cannula the cow's stomach wall 34 moves inwardly with respect to her skin 32 while the retainer ring 44 by its wing portions 50 contacting the inner surface of the stomach wall draws the cannula further through the cow's skin.

At a later time, after the bloat and conditions causing it has been relieved, the cannula is removed by manually grasping the outwardly projecting end thereof while on horseback. The flexibility of the wings 50 usually permit removal of the retainer ring 44 with the cannula or forces it off the pointed end of the cannula to pass through the animal's digestive tract.

Obviously the invention is susceptible to changes or alterations without defeating its practicability. Therefore, I do not wish to be confined to the preferred embodiment shown in the drawings and described herein.

I claim:

1. A bloat relief device, comprising:

an elongated open ended sleeve having a forward end portion and a rearward end portion;

an elongated plunger having one end axially slidably mounted for telescoping movement into the rearward end portion of said sleeve and having its other end projecting rearwardly of said sleeve, said one end of said plunger having a socket therein;

a cannula axially disposed within said sleeve forwardly of said plunger, said cannula having a sharpened end portion to facilitate its entry through the skin and stomach wall of an animal and having its other end portion nested by the socket in said plunger;

a ferrule surrounding said cannula adjacent each of its respective ends;

a stop washer longitudinally slidably surrounding said cannula between said ferrules, the periphery of said stop washer slidably contacting the inner wall surface of said sleeve; and, a retainer ring surrounding said cannula between its sharpened end portion and the adjacent said ferrule, said retainer ring having a plurality of flexible wing portions normally projecting laterally of the longitudinal axis of said cannula.

2. The device according to claim 1 and further including:

a stop ring surrounding said plunger for limiting its telescoping movement into said sleeve; and, a handle on the other end of said plunger.

* * * * *